(12) United States Patent
Karabelas et al.

(10) Patent No.: US 6,492,409 B1
(45) Date of Patent: *Dec. 10, 2002

(54) KINASE INHIBITORS

(75) Inventors: Kostas Karabelas, Lund (SE); Matti Lepistö, Lund (SE); Peter Sjö, Lund (SE)

(73) Assignee: Astrazeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/743,618

(22) PCT Filed: Jun. 22, 2000

(86) PCT No.: PCT/SE00/01336
§ 371 (c)(1),
(2), (4) Date: Jan. 12, 2001

(87) PCT Pub. No.: WO00/78750
PCT Pub. Date: Dec. 28, 2000

(30) Foreign Application Priority Data

Jun. 22, 1999 (SE) ................................................ 9902387

(51) Int. Cl.$^7$ .................. A61K 31/4178; C07D 403/04
(52) U.S. Cl. ..................................... 514/392; 548/312.1
(58) Field of Search ......................... 548/312.1; 514/392

(56) References Cited

U.S. PATENT DOCUMENTS

| | | | |
|---|---|---|---|
| 4,466,976 A | 8/1984 | Klose et al. ................ | 424/273 |
| 6,337,342 B1 * | 1/2002 | Karabelas et al. .......... | 514/392 |

FOREIGN PATENT DOCUMENTS

| | | |
|---|---|---|
| DE | 31 41 063 A1 | 4/1983 |
| JP | 64-7365 | 7/1990 |
| WO | WO 99/32483 | 7/1999 |

OTHER PUBLICATIONS

Pereira, et al., "Synthesis and Biological Evaluation of Monoindolyl and Indolocarbazolyl Oxazolones and Imidazolones", Chem. Pharm. Bull., vol. 45, No. 4, pp. 733–736, (1997).

Suvorov, et al., "Synthesis of 4(5)–(3–indoyl)imidazole", Chem. Abstract, 1970: 132619.

* cited by examiner

Primary Examiner—Laura L. Stockton
(74) Attorney, Agent, or Firm—Fish & Richardson P.C.

(57) ABSTRACT

The present invention relates to compounds of formula (I)

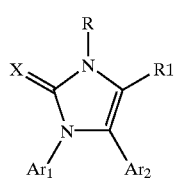

(I)

wherein:

$Ar_1$ or $Ar_2$ is an optionally substituted indole, and the other group is an optionally substituted aromatic or heteroaromatic group, suitably an optionally substituted bicyclic heteroaromatic group, preferably an optionally substituted indole, X is O or S, R is H, OH, $NH_2$, $C_{1-6}$alkyl, hydroxy$C_{1-6}$alkyl, amino$C_{1-6}$alkyl, and R1 is H, $C_{1-6}$alkyl, fluoro substituted $C_{1-6}$alkyl, phenyl, benzyl, carbo$C_{1-6}$alkoxy, carbobensyloxy, carbohydroxy, carbamoyl, or methyl(N-$C_{1-6}$alkylcarbamoyl)

and salts and solvates thereof and solvates of such salts, and the use of such compounds in medical therapies.

16 Claims, No Drawings

KINASE INHIBITORS

This application is a 371 of PCT/SE00/01336 filed Jun. 22, 2000.

FIELD OF THE INVENTION

The present invention relates to novel compounds which are protein kinase C inhibitors. methods for their preparation, intermediates therefor and pharmaceutical compositions comprising them.

BACKGROUND OF THE INVENTION

Protein kinase C (PKC) is a family of phospholipid-dependent serine/threonine-specific protein kinases which play an important role in cellular growth control, regulation and differentiation.

Since the activation of PKC has been implicated in several human disease processes, including various forms of cancer, different forms of inflammatory and/or immunological disorders as well as some neurological disorders, inhibition of PKC could be of therapeutic value in treating these conditions.

Several classes of compounds have been identified as PKC inhibitors, e.g. isoquinoline sulphonamides, sphingosine and related sphingolipids, indolocarbazoles and bisindolyl-maleimides.

EP 0 328 026 describes the use of certain bisindolylmaleimides, a class of compounds related to the indolocarbazoles, in medicaments for the treatment of various conditions.

Baskakow et al.; SU 389096; 1973 describes 1,5 substituted diphenyl imidazolones although these are not suggested to be of any therapeutic potential.

Although PKC inhibitors are described in the prior art, there is a need for specific anti-inflammatory and immuno suppressive compounds, which are suitable for oral administration, and for inhalation. Furthermore. there is a need for such compounds, which are more soluble and less colored than the presently known PKC inhibitors.

SUMMARY OF THE INVENTION

The present invention provides kinase inhibitors that are particularly PKC inhibitors. methods for their preparation and intermediates used for their preparation.

The kinase inhibitors of the present invention are surprisingly more soluble and less colored than the kinase inhibitors, especially the PKC inhibitors, known in the prior art.

The present invention also provides the use of the compounds of the present invention for the treatment of inflammatory, immunological, bronchopulmonary, cardiovascular, oncological or CNS-degenerative disorders.

Also provided by the present invention are pharmaceutical compositions comprising a compound according to the present invention, as active ingredient, together with a pharmaceutically acceptable adjuvant, diluent or carrier.

DETAILED DESCRIPTION OF THE INVENTION

The present invention provides compounds of formula (I):

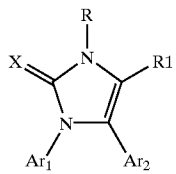

(I)

wherein:
  $Ar_1$ or $Ar_2$ is an optionally substituted indole, and the other group is an optionally substituted aromatic or heteroaromatic group, suitably an optionally substituted bicyclic heteroaromatic group, preferably an optionally substituted indole.
  X is O or S,
  R is H, OH, $NH_2$, $C_{1-6}$alkyl, hydroxy$C_{1-6}$alkyl, amino$C_{1-6}$alkyl, and
  R1 is H, $C_{1-6}$alkyl, fluoro substituted $C_{1-6}$alkyl, phenyl, benzyl, carbo$C_{1-6}$alkoxy, carbobensyloxy, carbohydroxy, carbamoyl, or methyl(N-$C_{1-6}$alkylcarbamoyl)
and salts and solvates thereof and solvates of such salts.
Preferred embodiments of formula (I) are compounds of formula (II), and (III)

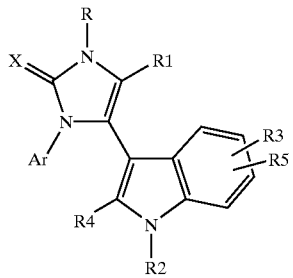

(II)

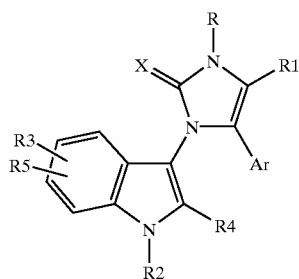

(III)

wherein:
  Ar is an optionally substituted aromatic or heteroaromatic group,
  X is O or S,
  R is H, OH, $NH_2$, $C_{1-6}$alkyl, hydroxy$C_{1-6}$alkyl, amino$C_{1-6}$alkyl,
  R1 is H, $C_{1-6}$alkyl, fluoro substituted $C_{1-6}$alkyl, phenyl, benzyl, carbo$C_{1-6}$alkoxy, carbobensyloxy, carbohydroxy, carbamoyl, or methyl(N-$C_{1-6}$alkylcarbamoyl),
  R2 is H, $C_{1-6}$alkyl, benzyl, $C_{1-3}$alkoxy substituted benzyl, hydroxy($C_{1-6}$)alkyl, hydroxy($C_{3-7}$)cycloalkyl, nitrile ($C_{1-6}$)alkyl, azido($C_{1-6}$)alkyl, amino($C_{1-6}$)alkyl, amino($C_{3-7}$)cycloalkyl, aminomethyl($C_{3-7}$)cycloalkyl, amino($C_{5-7}$)cycloalkenyl, (mono- or di-$C_{1-6}$alkyl) amino($C_{1-6}$)alkyl, benzylamino($C_{1-6}$)alkyl, (mono- or di-$C_{1-6}$alkyl) amino($C_{3-7}$)cycloalkyl, (mono- or di-$C_{1-6}$alkyl) aminomethyl($C_{3-7}$)cycloalkyl, (amino($C_{1-3}$)alkylphenyl)($C_{1-3}$)alkyl, amino($C_{1-3}$)alkylphenyl, guanidino($C_{1-6}$)alkyl, amidino($C_{1-6}$)alkyl, amidinothio($C_{1-6}$)alkyl, [N,N-di-($C_{1-6}$)alkyl]amidino($C_{1-6}$)alkyl, amidino($C_{1-3}$)alkylphenyl, [N,N-mono- or di-($C_{1-6}$)alkyl]amidino($C_{1-3}$)alkylphenyl, (N-benzyl)amidino($C_{1-3}$)alkylphenyl, (4-morpholinyl)imino($C_{1-3}$)alkylphenyl, benzimic acid methyl ester($C_{1-3}$)alkyl, hydroxy($C_{1-3}$)alkylamino ($C_{1-6}$)alkyl, carboxy($C_{1-3}$)alkylamino ($C_{1-6}$)alkyl, carboxymethyl($C_{1-3}$)alkylamino ($C_{1-6}$)alkyl, amino($C_{1-3}$)alkyloxy ($C_{2-6}$)alkyl, formamide($C_{1-6}$)alkyl, (N,N-dimethyl)imidoformamide($C_{1-6}$)alkyl, or a group of the formula

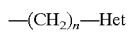
—(CH$_2$)$_n$—Het in which
n is an integer of 0–6;
Z is carbonyl or methylene;
Het is an optionally substituted 5- or 6-membered heterocyclic group,
R3 and R5 are each independently H, halogen, $C_{1-6}$alkyl, halo$C_{1-6}$alkyl, hydroxy$C_{1-6}$alkyl, $C_{1-6}$alkoxy, hydroxy, amino, nitro, nitrile, and
R4 is H, $C_{1-3}$alkyl or together with R2, forms an annulated ring which may be substituted by hydroxy$C_{1-3}$alkyl, amidinothio$C_{1-3}$alkyl, or amino$C_{1-3}$alkyl,
or a salt or solvate thereof or a solvate of a salt thereof.

Preferred embodiments of compounds of formula (II), and (III) are

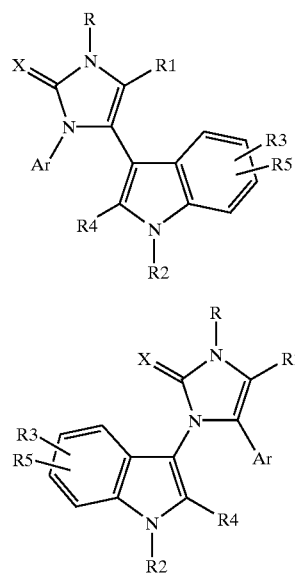

wherein:
Ar is an optionally substituted aromatic or heteroaromatic group,
X is O or S,
R is H, OH, NH$_2$, $C_{1-6}$alkyl, hydroxy$C_{1-6}$alkyl, amino$C_{1-6}$alkyl,
R1 is H, $C_{1-6}$alkyl, fluoro substituted $C_{1-6}$alkyl, phenyl, benzyl, carbo$C_{1-6}$alkoxy, carbobensyloxy, carbohydroxy, carbamoyl, or methyl(N-$C_{1-6}$alkylcarbamoyl),
R2 is H, $C_{1-6}$alkyl, halo$C_{1-6}$alkyl, bensyl, $C_{1-3}$alkoxy substituted bensyl, nitrile$C_{1-6}$alkyl, hydroxy$C_{1-6}$alkyl, amino$C_{1-6}$alkyl, (pyridinylmethyl)amino$C_{1-6}$alkyl, (mono- or di-$C_{1-6}$alkyl)amino$C_{1-6}$alkyl, (mono- or di-$C_{1-3}$haloalkyl)amino$C_{1-6}$alkyl, amino$C_{3-7}$cycloalkyl, (mono- or di-$C_{1-6}$alkyl)amino$C_{3-7}$cycloalkyl, (amino$C_{3-7}$cycloalkyl)$C_{1-3}$alkyl, (hydroxy$C_{1-6}$alkyl)amino$C_{1-6}$alkyl, (amino$C_{1-6}$alkyl)amino$C_{1-6}$alkyl, ($C_{1-6}$alkynyl)amino$C_{1-6}$alkyl, (bensyl)amino$C_{1-6}$alkyl, (mono- or di-$C_{1-3}$alkoxy substituted bensyl)amino$C_{1-6}$alkyl, (amino$C_{1-3}$alkylphenyl)$C_{1-3}$alkyl, (amino$C_{1-3}$alkylthiophenyl)$C_{1-3}$alkyl, (amino $C_{1-3}$alkylpyridinyl)$C_{1-3}$alkyl, guanidino $C_{1-6}$alkyl, (guanidino$C_{1-3}$alkylphenyl)$C_{1-3}$alkyl, amidino$C_{1-6}$alkyl or amidinothio$C_{1-6}$alkyl or a group of the formula

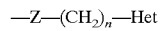
—Z—(CH$_2$)$_n$—Het in which
Z is carbonyl or methylene
n is an integer of 0–5, and
Het is an optionally substituted 5- or 6-membered heterocyclic group,
R3 and R5 are each independently H, halogen, $C_{1-6}$alkyl, halo$C_{1-6}$alkyl, hydroxy$C_{1-6}$alkyl, $C_{1-6}$alkoxy, hydroxy, amino, nitro, nitrile, and
R4 is H, $C_{1-3}$alkyl or together with R2, forms an annulated ring which may be substituted by hydroxy$C_{1-3}$alkyl, amidinothio$C_{1-3}$alkyl, or amino$C_{1-3}$alkyl,
and salts and solvates thereof and solvates of such salts.

For compounds of formula (II) and (III), the following independent preferences apply:
Ar is an optionally substituted bicyclic aromatic or an optionally substituted bicyclic heteroaromatic group,
R is H
X is O
R1 is H or methyl; or if a fluoro substituted $C_{1-6}$alkyl, is preferably CF$_3$,
when R4 is H, R2 is H, methyl, hydroxy$C_{1-6}$alkyl, amino$C_{1-6}$alkyl, (mono- or di-$C_{1-6}$alkyl)amino$C_{1-6}$alkyl, amino$C_{3-7}$cycloalkyl, (mono- or di-$C_{1-6}$alkyl)amino$C_{3-7}$cycloalkyl, guanidino $C_{1-6}$alkyl, amidino $C_{1-6}$ alkyl or amidinothio$C_{1-6}$alkyl,
when R2 and R4 together form an annulated ring, they together comprise 4 or 5 carbons,
R3 and R5 are independently H or methoxy.

In more preferred embodiments of formula (II) and (III), Ar comprises a single heteroatom selected from N, O and S.
In yet more preferred embodiments of formula (II) and (III), Ar is selected from benzothiophene, naphthyl, phenoxyphenyl, or an optionally substituted indolyl which if substituted is preferably substituted with aminopropyl, dimethylaminopropyl, aminobutyl, aminocyclopentyl, aminomethylbensyl, or amidinothiopropyl.

Preferred compounds according to the present invention include:
5-[1-(3-Aminopropyl)-3-indolyl]-1-(3-indolyl)-1,3-dihydroimidazol-2-one,
5-[1-(3-Aminopropyl)-3-indolyl]-1-(3-benzo[b]thoiphenyl-1,3-dihydroimidazol-2-one,
5-[1-(3-Aminopropyl)-3-indolyl]-1-(1-naphthyl)-1,3-dihydroimidazol-2-one, 5-[1-{3-(Aminomethyl)benzyl}-3-indolyl]-1-(3-indolyl)-1,3-dihydroimidazol-2-one, 5-[-1-(3-Aminopropyl)-3-indolyl]-1-(3-indolyl)-4-methyl-1,3-dihydroimidazol-2-one, 5-[1-(3-Amidinothiopropyl)-3-indolyl]-1-(3-indolyl)-1,3-dihydroimidazol-2-one, 5-{1-[3-(N,N-Dimethylamino)propyl]-3-indolyl}-1-(3-indolyl)-1,3-dihydroimidazol-2-one; and 5-[1-(3-Aminopropyl)-3-indolyl]-1-(3-indolyl)-4-phenyl-1,3-dihydroimidazol-2-one;

and salts and solvates thereof and solvates of such salts.

Salts of the compounds of formula (I) according to the invention are preferably pharmaceutically acceptable salts. Other salts may however be useful in the preparation of the compounds or in the preparation of pharmaceutically acceptable salts.

Pharmaceutically acceptable salts of compounds of the present invention are preferably those well known in the art as being suitable and are preferably acid addition salts and more preferably acetate salts or trifluoroacetate salts.

Solvates of the compounds or salts of the present invention are conveniently hydrates, such as monohydrates or dihydrates.

Compounds of the present invention include all pure stereoisomers and all mixtures thereof.

Preparation of the Compounds of the Invention

Compounds of formula (I) may be synthesised in the following ways:

(A) Compounds of formula (I) may be synthesised by converting a compound of formula (I) to a salt, especially a pharmaceutically acceptable salt, thereof, or vice versa; or converting a salt, especially a pharmaceutically acceptable salt, of a compound of formula (I) into a different salt, especially a pharmaceutically acceptable salt.

(B) Compounds of formula (I) may be synthesised by intramolecular condensation of a compound of formula (IV):

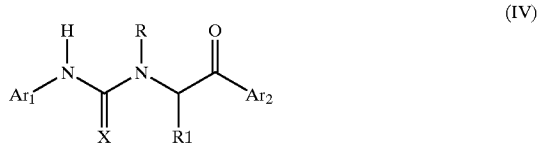

(IV)

in which X, R, R1, $Ar_1$ and $Ar_2$ are as defined for formula (I).

The condensation may be performed under acidic conditions, preferably using acetic acid or scandium(III) trifluoromethanesufonate, at a temperature in the range of from about 90° C. to about 130° C., suitably from 100° C. to 120° C. and preferably at about 100° C., for a period of time in the range of from about 5 min to about 6 h, suitably from 15 min to 3 h, preferably for about 1 h.

Compounds of formula (II) and (III) in which X is O may be synthesised by intramolecular condensation of a compound of formula (V) or (VI) respectively:

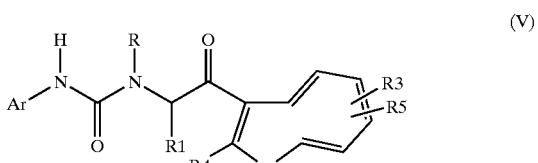

(V)

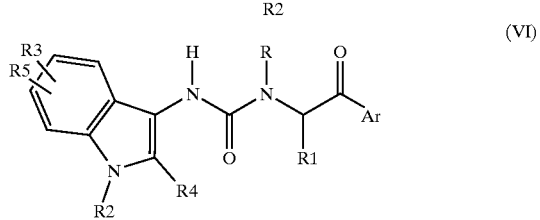

(VI)

in which Ar, R and R1–R5 are as defined for formula (II) and (III).

Compounds of formula (I), (II) or (III) carrying one or more functional groups which might be sensitive to or interfere with the reaction conditions in process (B), can be prepared using a corresponding compound of formula (I), (II) or (III) respectively, but in which the functional groups are suitably protected, followed by subsequent deprotection.

Functional groups that might be sensitive for or interfere with the reaction conditions in process (B), as well as suitable protecting groups and deprotecting methods, are evident to those skilled in the art.

Compounds of formula (II) or (III), in which at least one of R2 or Ar carries an amino, or hydroxy group; and pharmaceutically acceptable salts thereof, may be prepared by deprotecting a compound of formula (II) or (III), respectively, but in which at least one of R2 or Ar carries a protected amino or hydroxy group.

In the processes described above, the protecting groups and conditions for deprotection are well known to those skilled in the art. Suitable protecting groups for amino groups are e.g. phthaloyl groups and the deprotecting agent may be methylamine in e.g. water. The deprotecting step may be carried out in a suitable solvent, e.g. tetrahydrofuran at about 10–30° C., e.g. for about 5 hours. The hydroxy groups may be protected as their corresponding acetoxy groups and the deprotecting agent may be methylamine in e.g. water. The deprotecting step may be carried out in a suitable solvent, e.g. tetrahydrofuran at about 10–30° C., e.g. for about 16 hours.

The use of protecting groups is fully described in "Protective Groups in Organic Chemistry", edited by J. W. F. McOmie, Plenum Press (1973) and "Protective Groups in Organic Synthesis", $2^{nd}$ edition, T. W. Greene & P. G. M. Wutz, Wiley-Interscience (1991).

The starting materials for the above processes (A) and (B) may be made by the methods described herein and particularly by those methods set out in the Examples or by methods analogous thereto. Other conventional methods for making the starting materials will be evident to those skilled in the art.

Compounds of formula (V) and (VI) in which R2 is not H may be synthesised by alkylation with an optionally substituted alkylating agent, of compounds of formula (VII) and (VIII), respectively. The alkylating agent may be an alkyl halide, or an alkyl halide carrying a dialkyl amino group, or an alkylating agent carrying a protected amino or hydroxy group.

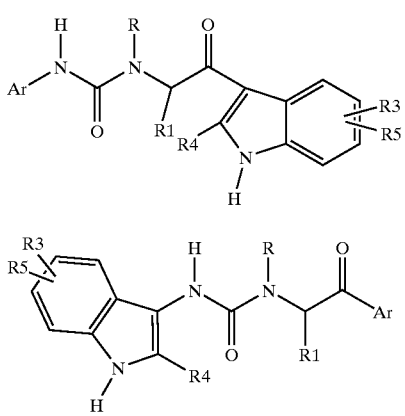

(VII)

(VIII)

in which Ar, R, R1–R5 are as defined for formula (II) and (III).

Compounds of formula (V) and (VI), in which Ar, R, R1–R5 are as defined for formula (II) and (III), provided that R2 is not H, may also be prepared by reaction of the appropriate isocyanate with a relevant alpha-ketoamine, wherein either the isocyanate or the alpha-ketoamine carries the R2 group, using standard techniques.

Compounds of formula (VII) and (VIII) may be prepared by reaction of the appropriate isocyanate with a relevant alpha-ketoamine using standard techniques.

Compounds of formula (II) in which X is O, R2 is alkyl and Ar is an indole, substituted on the indole nitrogen with an alkyl carrying an amino or hydroxy group, may be prepared by deprotecting a compound of formula (IX)

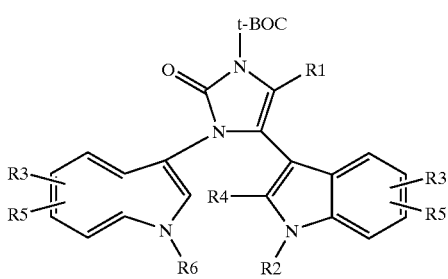

(IX)

in which R6 is an alkyl carrying a protected amino or hydroxy group, and R1, R3, R4 and R5 are as defined for formula (II).

The protecting groups and conditions for the deprotection are the same as mentioned earlier.

Compounds of formula (IX) may be prepared by selective removal of a Troc group from a compound of formula (X)

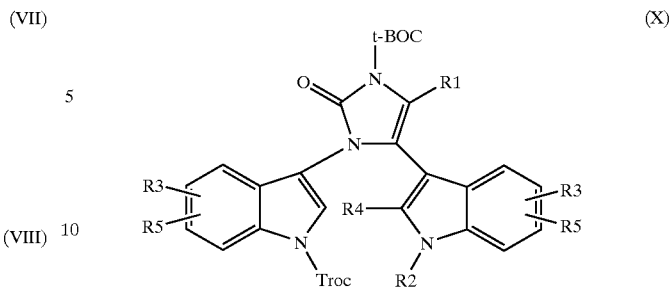

(X)

in which R2 is alkyl and R1, R3, R4 and R5 are as defined for formula (II),
followed by subsequent alkylation under standard conditions, with an alkyl carrying a protected amino or hydroxy group. Selective deprotection of the Troc group may be carried out with cadmium in acetic acid and DMF.

Compounds of formula (X) may be prepared by introducing a Boc group, under standard conditions, to a compound of formula (II) but in which R is H and the Ar group is a Troc protected indole. Such a compound is prepared from a compound of formula (V), but in which R is H and the Ar group is a Troc protected indole.

Persons skilled in the art will appreciate that, in order to obtain compounds of the invention in an alternative, and, on some occasions, more convenient, manner, the individual process steps mentioned herein may be performed in a different order, and/or the individual reactions may be performed at a different stage in the overall route. This will e.g. on factors such as the nature of other functional groups present in a particular substrate, the availability of key intermediates and the protecting group strategy (if any) to be adopted.

Prodrugs and Intermediates

It will also be appreciated by those skilled in the art that, although certain protected derivatives of compounds of formula (I), (II) and (III) which may be made prior to a final deprotection stage, may not possess pharmacological activity as such, they may be administered parenterally or orally and thereafter metabolized in the body to form compounds of the invention which are pharmacologically active. Such derivatives may therefore be described as "prodrugs". Moreover, certain compounds of formula (I), (II) and (III) may act as prodrugs of other compounds of formula (I), (II) and (III).

All prodrugs of compounds of formula (I) are included within the scope of the present invention.

Novel intermediates as described hereinbefore and their use in the manufacture of other compounds of the present invention also form part of the invention. Thus, according to a further aspect of the invention there is provided compounds of formulae (V) to (X) as defined hereinbefore, or protected derivatives of any of these compounds.

Medical and Pharmaceutical Use

Also provided according to the present invention are compounds of the present invention for use in medical therapy; the use of compounds of the present invention in the manufacture of medicaments for use in medical therapy, and more particularly in the treatment of the conditions described herein; and methods of medical therapy comprising the administration of a therapeutically effective amount of a compound of the present invention to an individual requiring such therapy.

The term 'medical therapy' as used herein is intended to include prophylactic, diagnostic and therapeutic regimens carried out in vivo or ex vivo on humans or other mammals.

The compounds of formula (I), (II) and (III) and salts, especially pharmaceutically acceptable salts, and solvates thereof, and solvates of such salts are useful because they demonstrate pharmacological activity. In particular they demonstrate activity as kinase inhibitors, especially PKC inhibitors, e.g. as is shown by their activity in the in vitro assays described in Granet, R. A. et al, Analyt. Biochem. 1987; 163, 458–463; Olsson, H. et al. Cell Signal 1989, 1, 405–410: and Chakravarthy, B. R. et al, Analyt. Biochem. 1991, 196, 144–150.

The compounds of the invention are indicated for use in the treatment of inflammatory, immunological, bronchopulmonary, cardiovascular, oncological or CNS-degenerative disorders; preferably for oral or topical treatment of inflammatory and/or immunological disorders, such as the oral or topical treatment of airway diseases involving inflammatory conditions, e.g. asthma, bronchitis; or atopic diseases, e.g. rhinitis or atopic dermatitis; inflammatory bowel diseases. e.g. Crohn's disease or colitis; autoimmune diseases e.g. multiple sclerosis, diabetes, atherosclerosis, psoriasis, systemic lupus erythematosus or rheumatoid arthritis; malignant diseases, e.g. skin or lung cancer; HIV infections or AIDS; or for inhibiting rejection of organs/transplants. The compounds of the invention are also indicated for use in treatment of heart failure, and in treatment of diabetic patients with macular edema or diabetic retinopathy.

Pharmaceutical Preparations

The dose of the compound to be administered will depend on the relevant indication, the age, weight and sex of the patient and may be determined by a physician. The dosage will preferably be in the range of from 0.01 mg/kg to 10 mg/kg.

The compounds may be administered topically, e.g. to the lung and/or the airways, in the form of solutions, suspensions, HFA aerosols or dry powder formulations, e.g. formulations in the inhaler device known as the Turbuhaler®; or systemically, e.g. by oral administration in the form of tablets, pills, capsules, syrups, powders or granules, or by parenteral administration, e.g. in the form of sterile parenteral solutions or suspensions, or by rectal administration, e.g. in the form of suppositories.

The compounds of the invention may be administered on their own or as a pharmaceutical composition comprising the compound of the invention in combination with a pharmaceutically acceptable diluent, adjuvant and/or carrier. Particularly preferred are compositions not containing material capable of causing an adverse, e.g. an allergic, reaction.

Dry powder formulations and pressurized HFA aerosols of the compounds of the invention may be administered by oral or nasal inhalation. For inhalation the compound is desirably finely divided. The finely divided compound preferably has a mass median diameter of less than 10 $\mu$m, and may be suspended in a propellant mixture with the assistance of a dispersant, such as a $C_8$–$C_{20}$ fatty acid or salt thereof, (e.g. oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, e.g. a mono-, di- or polysaccharide, a sugar alcohol, or another polyol. Suitable carriers are sugars, e.g. lactose, glucose, raffinose, melezitose, lactitol, maltitol, trehalose, sucrose. mannitol; and starch. Alternatively the finely divided compound may be coated by another substance. The powder mixture may also be dispensed into hard gelatin capsules, each containing the desired dose of the active compound.

Another possibility is to process the finely divided powder into spheres which break up during the inhalation procedure. This spheronized powder may be filled into the drug reservoir of a multidose inhaler, e.g. that known as the Turbuhaler® in which a dosing unit meters the desired dose which is then inhaled by the patient. With this system the active compound, with or without a carrier substance, is delivered to the patient.

For oral administration the active compound may be admixed with an adjuvant or a carrier, e.g. lactose, saccharose, sorbitol, mannitol; a starch, e.g. potato starch, corn starch or amylopectin; a cellulose derivative; a binder, e.g. gelatin or polyvinylpyrrolidone, and/or a lubricant, e.g. magnesium stearate, calcium stearate, polyethylene glycol, a wax, paraffin, and the like, and then compressed into tablets. If coated tablets are required, the cores, prepared as described above, may be coated with a concentrated sugar solution which may contain e.g. gum arabic, gelatin, talcum, titanium dioxide, and the like. Alternatively, the tablet may be coated with a suitable polymer dissolved in a readily volatile organic solvent.

For the preparation of soft gelatin capsules, the compound may be admixed with e.g. a vegetable oil or polyethylene glycol. Hard gelatin capsules may contain granules of the compound using either the above mentioned excipients for tablets. Also liquid or semisolid formulations of the drug may be filled into hard gelatin capsules.

Liquid preparations for oral application may be in the form of syrups or suspensions, for example solutions containing the compound, the balance being sugar and a mixture of ethanol, water, glycerol and propylene glycol. Optionally such liquid preparations may contain coloring agents, flavoring agents, saccharine and/or carboxymethylcellulose as a thickening agent or other excipients known to those skilled in art.

The compounds of the invention may also be administered in conjunction with other compounds used for the treatment of the above conditions.

EXAMPLES

The following Examples are intended to illustrate, but in no way limit the scope of the invention.

GENERAL METHODS

All reactions were performed in dried glassware in an argon atmosphere at room temperature, unless otherwise noted. Tetrahydrofuran (THF) was distilled from sodium benzophenone ketyl under $N_2$ prior to use. N,N-Dimethyl formamide (DMF) was distilled from calcium hydride and stored over molecular sieves. All other solvents and reagents were used as received.

Chromatography, unless otherwise stated, was carried out using a Chromatotron® (a centrifugally accelerated, radial preparative chromatograph), the plates used were prepared using Merck Silica Gel $PF_{254}$ containing gypsum.

$^1$H-NMR spectra were recorded on a Varian Inova-400 or Unity-500+ instrument. The central solvent peak of chloroform-d ($\delta_H$ 7.27 ppm), dimethylsulfoxide-$d_6$ ($\delta_H$ 2.50 ppm) or methanol-$d_4$ ($\delta_H$ 3.35 ppm) were used as internal references. Low-resolution mass spectra were recorded on an Autospec-Q, Fisons Analytical, double focusing sector instrument equipped with a LSIMS interface. Low resolution mass spectra were also obtained on a Hewlett Packard 1 100 LC-MS system equipped with an APCI ionization chamber.

3-(Azidocarbonyl)-1-(2,2,2-trichloroethoxycarbonyl)indole was prepared in 52% yield following the procedure outlined by Suvorov et al. Khimiya Gereotsiklicheskikh Soedinenii, 8 (1975) 1099–1105.

$^1$H-NMR (400 MHz, DMSO-$d_6$): δ 5.27 (2H, s), 7.43 (1H, t, J 7.4 Hz), 7.49 (1H, t, J 7.6 Hz), 8.12 (1H, d, J 7.8 Hz), 8.16 (1H, d, J 8.0 Hz), 8.26 (1H, s).

Example 1

1-(3-Indolyl)-5-(1-methyl-3-indolyl)-1,3-dihydroimidazol-2-one a) 3-{3-[2-(3-Indolyl)-2-oxoethyl]ureido}-1-(ethoxycarbonyl)indole A solution of 3-(azidocarbonyl)-1-(ethoxycarbonyl)indole prepared according to Suvorov (ibid) (1.32 g, 5.12 mmol) in benzene (25 ml) was heated to reflux for 7 hours. After cooling to room temperature. THF (25 ml) and [2-(3-indolyl)-2-oxoethyl]ammonium bromide [Oikawa,Y. et al. Heterocycles 12 (1979) 1457–1462] (1.31 g, 5.12 mmol) were added immediately followed by ethyldiisopropylamine (0.89 ml, 5.12 mmol). After stirring for 1.5 hours the formed precipitate was removed by filtration and washed with THF followed by water. The sub-title compound (1.65 g, 79%) was obtained as a white solid after drying.

$^1$H-NMR (500 MHz, DMSO-$d_6$): δ 1.38 (3H, t, J 7.3 Hz), 4.41 (2H, q, J 7.3 Hz), 4.60 (2H, d, J 5.0 Hz), 6.71 (1H, t, J 5.0 Hz), 7.18–7.27 (2H, m), 7.33 (1H, t, J 7.7 Hz), 7.39 (1H, t, J 7.7 Hz), 7.50(1H, d, J 6.6 Hz), 7.72 (1H, d, J 7.5 Hz), 7.83 (1H, s), 8.11 (1H, d, J 8.2 Hz), 8.19 (1H, d, J 6.7 Hz), 8.47 (1H, d, J 3.1 Hz), 9.12 (1H, s), 12.05 (1H, br s, indole NH).

FAB-MS: m/z 429 [MNa+], 405 [MH+].

b) 3-{3-[2-(1-Methyl-3-indolyl)-2-oxoethyl]ureido}-1-(ethoxy-carbonyl)indole

The product of step a) (1.50 g, 3.71 mmol) and $K_2CO_3$ (2.05 g, 14.8 mmol) were mixed in dry DMF (25 ml). Methyl iodide (0.25 ml, 4.08 mmol) was added and the reaction allowed to proceed until HPLC showed that the starting material had been consumed, generally after about 3 hours. Aqueous acetic acid (1M, 50 ml) and ethyl acetate (50 ml) were added and the phases separated whereupon the sub-title product precipitated. The organic phase containing the precipitate was washed with water (2×25 ml), filtered off and washed with water to give the sub-title product (0.96 g, 62%) as a white solid after drying.

$^1$H-NMR (500 MHz, DMSO-$d_6$): δ 1.37 (3H, t, J 7.2 Hz), 3.90 (3H, s), 4.41 (2H, q, J 7.1 Hz), 4.57 (2H, d, J 5.2 Hz), 6.73 (1H, br t, J 5.0 Hz), 7.26 (1H, t, J 7.2 Hz), 7.28–7.34 (3H, m), 7.39 (1H, t, J 7.6 Hz), 7.57 (1H, d, J 7.9 Hz), 7.72 (1H, d, J 7.9 Hz), 7.82 (1H, s), 8.10 (1H, br d, J 8.6 Hz), 8.19 (1H, d, J 7.8 Hz), 8.50 (1H, s), 9.13 (1H, s).

c) 1-[1-(Ethoxycarbonyl)-3-indolyl]-5-(1-methyl-3-indolyl)-1,3-dihydroimidazol-2-one The product of step b) (2.63 g, 6.29 mmol) was suspended in acetic acid (30.0 ml) and heated to 110° C. until all the starting material has been consumed after about 3 hours. The solvent was removed and the residue titurated with diethyl ether to give the sub-title compound (1.84 g, 74%) as an off-white solid.

$^1$H-NMR (400 MHz, DMSO-$d_6$): δ 1.38 (3H, t, J 7.0 Hz), 3.57 (3H, s), 4.44 (2H, q, J 7.0 Hz), 6.77 (1H, br d, J 2.1 Hz), 6.94 (1H, s), 7.00 (1H, t, J 7.3 Hz), 7.10–7.17 (2H, m), 7.21 (1H, d, J 7.6 Hz), 7.30–7.36 (2H, m), 7.57 (1H, d, J 8.0 Hz), 7.78 (1H, s), 8.09 (1H, d, J 8.1 Hz), 10.44 (1H, s).

FAB-MS: 401 [MH+], 801 [MH2+].

d) The sub-title product of step c) (0.17 g, 0.44 mmol) was dissolved in THF (3 ml) and aqueous methyl amine (40%, 3 ml) and stirred for 30 minutes. The solvent was removed and the product precipitated from diethyl ether to give the title compound (0.14 g, 94%) as a slightly brown solid.

$^1$H-NMR (400 MHz, DMSO-$d_6$): δ 3.53 (3H, s), 6.68 (1H, s), 6.71 (1H, s), 6.93 (1H, t, J 7.6 Hz), 6.98 (1H, t, J 7.6 Hz), 7.08 (1H, t, J 7.0 Hz), 7.11 (1H, t, J 7.0 Hz), 7.18 (1H, d, J 7.8 Hz), 7.32 (1H, d, J 8.1 Hz), 7.35–7.39 (2H, m), 7.56 (1H, d, J 7.9 Hz), 10.24 (1H, s), 11.17(1H, br s).

FAB-MS: m/z 329 [MH+], 657 [MH2+].

Example 2

1,5-Bis-(3-indolyl)-1,3-dihydroimidazol-2-one a) 1-(1-Ethoxycarbonyl-3-indolyl)-5-(3-indolyl)-1,3-dihydroimidazol-2-one The product of Example 1 a) (0.90 g, 2.23 mmol) was suspended in acetic acid (20.0 ml) and heated to 110° C. until all the starting material had been consumed after about 3.5 hours. The solvent was removed and the residue chromatographed, eluting with $CH_2Cl_2$-MeOH (100:10) to give the title compound (0.69 g, 80%) obtained as an off-white solid.

$^1$H-NMR (500 MHz, DMSO-$d_6$): δ 1.37 (3H, t, J 7.1 Hz), 4.44 (2H, q, J 7.1 Hz), 6.80 (1H, d, J 2.4 Hz), 6.82 (1H, d, J 2.6 Hz), 6.99 (1H, t, J 7.6 Hz), 7.07 (1H, t, J 7.6 Hz), 7.14 (1H, t, J 7.4 Hz), 7.19 (1H, d, J 7.8 Hz), 7.29 (1H, d, J 7.9 Hz), 7.32 (1H, d, J 7.7 Hz), 7.60 (1H, d, J 7.9 Hz), 7.80 (1H, s), 8.10 (1H, d, J 8.4 Hz), 10.42 (1H, br d, J 2.2 Hz), 10.94 (1H, br s).

FAB-MS: m/z 387 [MH+].

The product of step a) (0.055 g, 0.143 mmol) was dissolved in THF (1 ml) and aqueous methylamine (40%, 1 ml). The reaction was complete after 1 hour. Solvent removal followed by chromatography on silica eluting with dichloromethane—methanol (100:10), save the title compound (0.028 g, 63%) as a slightly brown solid.

$^1$H-NMR (400 MHz, DMSO-$d_6$): δ 6.53 (1H, d, J 2.7 Hz), 6.76 (1H, d, J 2.5 Hz), 6.93 (1H, t, J 7.3 Hz), 6.98 (1H, t, J 7.2 Hz), 7.06 (1H, t, J 7.6 Hz), 7.09 (1H, t, J 7.7 Hz), 7.17 (1H, d, J 8.1 Hz), 7.26 (1H, d, J 7.3 Hz), 7.39 (1H, d, J 8.3 Hz), 7.41 (1H, d, J 2.9 Hz), 7.62 (1H, d, J 7.9 Hz), 10.23 (1H, br d, J 2.1 Hz), 10.86 (1H, br s), 11.23 (1H, br s).

FAB-MS: m/z 315 [MH+].

Example 3

1-[1-(4-Aminobutyl)-3-indolyl]-5-(1-methyl-3-indolyl)-1,3-dihydroimidazol-2-one Trifluoroacetic Acid Salt a) 3-{3-[2-(3-Indolyl)-2-oxoethyl]ureido}-1-(2,2,2-trichloroethoxycarbonyl)indole The sub-title product was prepared in 71% yield as a white solid following the procedure of Example 1 a) starting from 3-(azidocarbonyl)-1-(2,2,2-trichloroethoxycarbonyl)indole (see General Methods).

$^1$H-NMR (400 MHz, DMSO-$d_6$): δ 4.58 (2H, d, J 5.2 Hz), 5.18 (2H, s), 6.70 (1H, t, J 5.0 Hz), 7.14–7.21 (2H, m), 7.34 (1H, t, J 7.4 Hz), 7.39 (1H, t, J 8.1 Hz), 7.43–7.48 (1H, m), 7.72 (1H, d, J 7.6 Hz), 7.89 (1H, s), 8.09–8.17 (2H, m), 8.43 (1H, br d, J 2.6 Hz), 9.19 (1H, s), 12.01 (1H, br s, indole NH).

b) 3-{3-[2-(1-Methyl-3-indolyl)-2-oxoethyl]ureido}-1-(2,2,2-trichloroethoxycarbonyl)indole The sub-title compound, obtained as a white solid, was prepared in 63% yield following the procedure of Example I b) starting from the product of step a).

¹H-NMR (400 MHz, DMSO-d₆): δ 3.89 (3H, s), 4.59 (2H, d, J 5.0 Hz), 5.23 (2H, s), 6.84 (1H, t, J 5.0 Hz, NH), 7.26 (1H, t, J 7.2 Hz), 7.33 (1H, t, J 6.9 Hz), 7.39 (1H, t, J 7.1 Hz), 7.44 (1H, t, J 7.7 Hz), 7.57 (1H, d, J 8.1 Hz), 7.79 (1H, d, J 7.6 Hz), 7.93 (1H, s), 8.16 (1H, d, J 8.2 Hz), 8.20 (1H, d, J 7.7 Hz), 8.51 (1H, s), 9.30 (1H, s).

c) 5-(1-Methyl-3-indolyl)-1-[1-(2,2,2-trichloroethoxycarbonyl)-3-indolyl]-1,3-dihydroimidazol-2-one The sub-title product, obtained as an off-white solid, was prepared in 86% yield following the procedure in Example 1 c) starting from the product of step b). The product was precipitated from diethyl ether.

¹H-NMR (400 MHz, DMSO-d₆): δ 3.60 (3H, s), 5.24 (2H, s), 6.77 (1H, s), 6.97 (1H, t, J 7.8 Hz), 7.03 (1H, s), 7.11 (1H, t, J 7.8 Hz), 7.21 (1H, t, J 7.4 Hz), 7.30–7.41 (3H, m), 7.49 (1H, d, J 8.0 Hz), 7.70 (1H, s), 8.13 (1H, d, J 8.3 Hz), 10.48 (1H, s).

FAB-MS: mi/z 503 [MH+].

d) 1-(tert-Butoxycarbonyl)-4-(1-methyl-3-indolyl)-3-[1(2,2,2-trichloroethoxycarbonyl)-3-indolyl]-1,3-dihydroimidazol-2-one The product of step c) (0.10 g, 0.20 mmol), di-tert-butyl dicarbonate (0.054 g, 0.25 mmol) and a catalytic amount of 4-N,N-dimethylaminopyridine in dry THF (3 ml) was stirred for 5 minutes at room temperature. Removal of the solvent and chromatographic purification on silica, eluting with heptane—ethyl acetate (60:40), gave the sub-title product (0.11 g, 94%) as a slightly brown solid.

¹H-NMR (500 MHz, CDCl₃): δ 1.66 (9H, s), 3.59 (3H, s), 5.01 (2H, s), 6.66 (1H, s), 7.04 (1H, s), 7.16 (1H, dt, J 2.5, 6.0 Hz), 7.21 (1H, t, J 7.6 Hz), 7.25–7.27 (2H, m), 7.33–7.42 (2H, m), 7.67 (1H, d, J 7.9 Hz), 7.71 (1H, s), 8.23 (1H, br d, J 8.2 Hz).

FAB-MS: m/z 602 [MH+], 625 [MNa+].

e) 1-(tert-Butoxycarbonyl)-4-(1-methyl-3-indolyl)-3-(3-indolyl)-1,3-dihydroimidazol-2-one The product of step d) (0.21 g, 0.34 mmol), zinc powder (0.23 g, 3.44 mmol) and cadmium(II) chloride (0.020 g, 0.086 mmol) was suspended in DMF (4 ml) and acetic acid (4 ml). The suspension was stirred for 1 hour at room temperature, ethyl acetate (10 ml) and water (20 ml) were added and the phases separated. The organic phase was washed with water (3×5 ml), dried over Na₂SO₄. Solvent removal followed by chromatographic purification on silica, eluting with ethyl acetate, gave the sub-title product (0.12 g, 81%) as a colourless solid.

¹H-NMR (500 MHz, CDCl₃): δ 1.69 (9H, s), 3.40 (3H, s), 6.32 (1H, s), 6.84 (1H, br t, J 2.3 Hz), 6.92–7.00 (2H, m), 7.04–7.09 (2H, m), 7.16–7.26 (3H, m), 7.29–7.33 (1H, m), 7.75 (1H, dt, J 1.4, 2.3 Hz), 9.43 (1H, br s).

FAB-MS: m/z 428 [MH+], 451 [MNa+].

f) 1-(tert-Butoxycarbonyl)-3-{1-[4-(1,3-Dioxo-1,3-dihydroisoindol-2-yl)-butyl]-3-indolyl}-4-(1-methyl-3-indolyl)-2,3-dihydroimidazole-2-one The product of step e) (0.034 g, 0.080 mmol), N-(4-bromobutyl)phthalimide (0.028 g, 0.10 mmol) and sodium hydride (95%, 0.0024 g, 0.10 mmol) was dissolved in dry DMF (0.5 ml). After stirring at room temperature for 1.5 hour HPLC shows complete reaction. The reaction was quenched by addition of aqueous acetic acid (1 M, 2 ml) and ethyl acetate (2 ml). The phases were separated and the organic phase washed with water (1×2 ml). Solvent removal followed by chromatographic purification on silica, eluting with heptane—ethyl acetate (20:80), furnished the sub-title product (0.019 g, 38%) as a slightly brown solid.

¹H-NMR (500 MHz, CDCl₃): δ 1.61 (9H, s), 1.64–1.79 (4H, m), 3.56 (3H, s), 3.67 (2H, t, J 6.5 Hz), 3.71 (2H, t, J 6.7 Hz), 6.87 (1H, s), 6.97 (1H, s), 7.02 (1H, t, J 7.6 Hz), 7.10–7.18 (2H, m), 7.31 (1H, t, J 7.1 Hz), 7.35 (1H, d, J 8.2 Hz), 7.60 (1H, d, J 8.1 Hz), 7.77 (1H, s), 7.80–7.88 (4H, m), 8.06 (1H, d, J 8.3 Hz).

FAB-MS: m/z 629 [MH+].

g) The product of step f) (0.018 g, 0.029 mmol) was dissolved in THF (0.25 ml) and aqueous methyl amine (40%, 0.25 ml) and stirred for 1 hour. HPLC showed complete deprotection. Solvent removal and purification by preparative HPLC, (C18-reversed phase, acetonitrile—water—trifluoroacetic acid (30:70:0.1) gave the title product (0.0082 g, 54%) as pale yellow solid after freez drying.

¹H-NMR (400 MHz, CD₃OD): δ 1.79 (2H, p, J 7.8 Hz), 1.95 (2H, p, J 7.8 Hz), 3.04 (2H, t, J 7.8 Hz), 3.50 (3H, s), 3.89 (2H, t, J 6.8 Hz), 6.48 (1H, s), 7.00 (1H, t, J 7.9 Hz), 7.05 (1H, t, J 7.0 Hz), 7.13–7.19 (2H, m), 7.24 (1H, d, J 8.0 Hz), 7.26–7.30 (2H, m), 7.42 (1H, d, J 8.2 Hz), 7.62 (1H, d, J 8.0 Hz).

FAB-MS: m/z 400 [MH+].

Example 4

5-[1-(3-Aminopropyl)-3-indolyl]-1-(3-indolyl)-1,3-dihydroimidazol-2-one Trifluoroacetic Acid Salt a) 3-[3-(2-{1-[3-(1,3-Dioxo-1,3-dihydroisoindol-2-yl)-propyl]-3-indolyl}-2-oxo-ethyl)ureido]-1-(ethoxycarbonyl)indole The sub-title product, obtained as a white solid, was prepared in 63% yield following the procedure of Example 1 b) starting from the product of Example 1 a) and N-(3-bromopropyl)phthalimide.

¹H-NMR (400 MHz, DMSO-d₆): δ 1.37 (3H, t, J 7.1 Hz), 2.18 (2H, p, J 7.1 Hz), 3.66 (2H, t, J 6.7 Hz), 4.34–4.44 (4H, m), 4.57 (2H, d, J 5.0 Hz), 6.71 (1H, br t, J 5.0 Hz), 7.22–7.40 (4H, m), 7.66 (1H, d, J 8.0 Hz), 7.71 (1H, d, J 7.7 Hz), 7.80–7.89 (5H, m), 8.09 (1H, br d, J 8.2 Hz), 8.17 (1H, d, J 8.0 Hz), 8.57 (1H, s), 9.12 (1H, s).

FAB-MS: m/z 592 [MH+].

b) 5-(1-[3-{1,3-Dioxo-1,3-dihydroisoindol-2-yl}-propyl]-3-indolyl)-1-[1-(ethoxycarbonyl)-3-indolyl]-1,3-dihydroimidazol-2-one The sub-title product, obtained as an off-white solid, was prepared in 99% yield following the procedure of Example 1 c) starting from the product of step a). The product was precipitated from diethyl ether.

¹H-NMR (500 MHz, DMSO-d₆): δ 1.30 (3H, t, J 7.1 Hz), 1.69 (2H, p, J 6.6 Hz), 2.91 (2H, t, J 6.8 Hz), 4.01 (2H, t, J 6.5 Hz), 4.35 (2H, q J 7.1 Hz), 6.83 (1 H, d, J 2.4 Hz), 7.02 (1H, t, J 7.1 Hz), 7.03–7.09 (2H, m), 7.10 (1H, s), 7.13 (2H, t, J 7.5 Hz), 7.40 (1H, d, J 8.2 Hz), 7.66 (1H, d, J 8.0 Hz), 7.80 (1H, s), 7.85 (4H, s), 7.90 (1H, d, J 8.4 Hz), 10.46 (1H, s).

FAB-MS: 574 [MH+], 1147 [MH2+].

c) The title product, obtained as an off-white solid, was prepared in 66% yield following the procedure of Example 3 f) starting from the product of step b). The product was purified by chromatography on silica, eluting with dichloromethane—methanol—ammonium hydroxide (80:20:2), the free base was treated with diluted trifluoroacetic acid before lyophilisation.

¹H-NMR (500 MHz, DMSO-d₆): δ 1.76 (2H, p, J 7.3 Hz), 2.47 (2H, p, J 6.7 Hz), 4.00 (2H, t, J 6.8 Hz), 6.71 (1H, s), 6.73 (1H, d, J 2.5 Hz), 6.90 (1H, t, J 7.1 Hz), 7.0 (1H, t, J 7.4 Hz), 7.06 (1H, t, J 7.4 Hz), 7.10–7.14 (2H, m), 7.36–7.39 (2H, m), 7.41 (1H, d, J 8.3 Hz), 7.58 (1H, d, J 8.1 Hz), 7.64 (3H, br s, NH₃), 10.29 (1H, s), 11.17 (1H, s).

FAB-MS: m/z 372 [MH+].

Example 5

5-[1-(3-Aminopropyl)-3-indolyl]-1-(1-naphthyl)-1,3-dihydroimidazol-2-one Trifluoroacetic Acid Salt a) 1-[2-(3-Indolyl)-2-oxoethyl]-3-(1-naphthyl)urea

[2-(3-indolyl)-2-oxoethyl]ammonium bromide (2.00 g, 7.84) was suspended in dry THF (20 ml). Ethyldiisopropylamine (1.40 ml, 7.84 mmol) was added followed by 1-naphthyl-isocyanate (1.13 ml, 7.84 ml). After stirring for 1 hour the formed precipitate was removed by filtration and washed with THF followed by water to give the sub-title product (2.33 g, 87%) as a white solid after drying.

$^1$H-NMR (400 MHz, DMSO-d$_6$): δ 4.63 (2H, s), 7.11 (1H, br t, J 4.8 Hz), 7.19–7.27 (2H, m), 7.43 (1 H, t, J 8.0 Hz), 7.48–7.60 (4H, m), 7.90 (1 H, d, J 7.7 Hz), 8.05 (1H, d, J 7.7 Hz), 8.18–8.25 (2H, m), 8.49 (1H, br d, J 2.9 Hz), 8.94 (1H, s), 12.06 (1H, br s).

FAB-MS: m/z 344 [MH+].

b) 1-[2-(1-[3-(1,3-Dioxo-1,3-dihydroisoindol-2-yl)-propyl]-3-indolyl)-2-oxoethyl]-3-(1-naphthyl)urea The sub-title product, obtained as a white solid, was prepared in 85% yield following the procedure of Example 1 b) starting from the product of step a) and N-(3-bromopropyl)-phthalimide.

$^1$H-NMR (400 MHz, DMSO-d$_6$): δ 2.19 (2H, p, J 6.9 Hz), 3.67 (2H, t, J 6.7 Hz), 4.37 (2H, t, J 7.3 Hz), 4.61 (2H, d, J 4.8 Hz), 7.11 (1H, br t, J 4.8 Hz), 7.22–7.32 (2H, m), 7.42 (1H, t, J 8.0 Hz), 7.49–7.59 (3H, m), 7.66 (1H, d), 7.80–7.91 (5H, m), 8.04 (1H, d), 8.18–8.22 (2H, m), 8.58 (1H, s), 8.93 (1H, s).

FAB-MS: m/z 531 [MH+].

c) 5-[1-(1,3-Dioxo-1,3-dihydro-isoindol-2-yl)-propyl]-3-indolyl]-1-(1-naphthyl)-1,3-dihydroimidazol-2-one The sub-title product, obtained as an off-white solid, was prepared in 60% yield following the procedure of Example 1 c) starting from the product of step b).

$^1$H-NMR (400 MHz, DMSO-d$_6$): δ 1.68 (2H, p, J 6.7 Hz), 3.10 (2H, dp, J 7.1, 38.8 Hz), 3.91 (2H, t, J 6.7 Hz), 6.47 (1H, s), 6.68 (1H, d, J 2.4 Hz), 6.98 (1H, t, J 7.4 Hz), 7.08 (1H, t, J 7.8 Hz), 7.31–7.45 (3H, m), 7.46–7.62 (4H, m), 7.81–7.91 (6H, m), 10.46 (1H, br s).

FAB-MS: m/z 513 [MH+].

d) The title compound, obtained as an off-white solid, was prepared in 77% yield following the product of Example 3 f) starting from the product of step c). The product was purified by chromatography on silica, eluting with dichloromethane—methanol—ammonium hydroxide (80:20:2).

$^1$H-NMR (400 MHz, CD$_3$OD): δ 1.77 (2H, p, J 7.4 Hz), 2.29–2.44 (2H, m), 3.88 (2H, t, J 6.7 Hz), 6.26 (1H, s), 6.87 (1H, s), 7.05 (1H, t, J 7.2 Hz), 7.14 (1H, t, J 7.2 Hz), 7.26 (1H, d, J 8.3 Hz), 7.37–7.54 (4H, m), 7.62 (2H, d, J 8.1 Hz), 7.90 (1H, d, J 8.1 Hz), 7.93 (1H, d, J 8.1 Hz).

FAB-MS: m/z 383 [MH+].

Example 6

5-[1-(3-Aminopropyl)-3-indolyl]-1-(3-benzo[b]thiophenyl)-1,3-dihydroimidazol-2-one Acetic Acid Salt a) 1-[2-(3-Indolyl)-2-oxoethyl]-3-(3-benzo[b]thiophenyl)urea

The sub-title compound was prepared in 85% yield as a white solid following the procedure of Example 1 a) starting from 3-azidocarbonyl-benzo[b]thiophene [Galvez. C. et al. Synthesis (1983) 932–933].

$^1$H-NMR (400 MHz, DMSO-d$_6$): δ 4.63 (2H, d, J 4.9 Hz), 6.88 (1H, t, J 4.9 Hz), 7.19–7.22 (2H, m), 7.34–7.54 (4H, m), 7.95 (2H, t, J 8.0 Hz), 8.17–8.22 (1H, m), 8.49 (1H, d, J 2.9 Hz), 9.24 (1H, s), 12.06 (1H, s).

b) 3-[3-(2-{1-[3-(1,3-Dioxo-1,3-dihydroisoindol-2-yl)-propyl]-3-indolyl}-2-oxo-ethyl)ureido]-benzo[b]thiophene The sub-title product, obtained as a white solid, was prepared in quantitative yield following the procedure of Example 1 b) starting from the product of step a) and N-(3-bromopropyl)phthalimide.

$^1$H-NMR (500 MHz, DMSO-d$_6$): δ 2.19 (2H, p, J 7.1 Hz), 3.66 (2H, t, J 6.9 Hz), 4.37 (2H, t, J 7.1 Hz), 4.60 (2H, d, J 5.1 Hz), 6.87 (1H, t, J 5.1 Hz), 7.26 (2H, dt, J 7.6, 20.4 Hz), 7.39 (1H, t, J 7.5 Hz), 7.46 (1H, t, J 7.9 Hz), 7.62 (1H, s)7.66 (1H, d, J 7.9 Hz), 7.81–7.89 (4H, m) 7.94 (2H, t, J 7.7 Hz), 8.18 (1H, d, J 7.1 Hz), 8.58 (1H, s), 9.23 (1H, s).

FAB-MS: m/z 537.1 [MH+].

c) 5-[1-(1,3-Dioxo-1,3-dihydroisoindol-2-yl)-propyl]-3-indolyl]-1-(3-benzo[b]thiophenyl)-1,3-dihydroimidazol-2-one The sub-title product, obtained as an off-white solid, was prepared in 30% yield following the procedure of Example 1 c) starting from the product of step b).

$^1$H-NMR (500 MHz, CDCl$_3$): δ 1.89 (2H, p, J 6.7 Hz), 3.29 (2H, t, J 6.7 Hz), 3.94 (2H, t, J 6.7 Hz), 6.53 (1H, s), 6.66 (H, s), 7.12 (1H, t, J 7.5 Hz), 7.15–7.32 (4H, m), 7.55 (1H, s), 7.61 (2H, dd, J 8.1, 12.2 Hz), 7.70–7.78 (3H, m), 7.82–7.90 (2H, m), 10.93 (1H, s).

FAB-MS: m/z 519.1 [MH+].

d) The title compound, obtained as an off-white solid, was prepared in 50% yield following the procedure of Example 3 f) starting from the product of step c). The product was purified by chromatography on silica, eluting with dichloromethane—methanol—ammonium hydroxide (80:20:2).

$^1$H-NMR (500 MHz, DMSO-d$_6$): δ 1.50 (2H, p, J 6.7 Hz), 1.86 (3H, s), 2.10 (2H, t, J 6.7 Hz), 3.97 (2H, t, J 6.7 Hz), 6.63 (1H, s), 6.83 (1H, s), 6.99 (1H, t, J 7.1 Hz), 7.10 (1H, t, J 7.1 Hz), 7.28 (1H, t, J 7.6 Hz), 7.32–7.40 (3H, m), 7.57 (1H, d, J 7.9 Hz), 7.82 (1H, s), 7.98 (1H, s, J 7.9 Hz), 10.44 (br s, 1H).

FAB-MS: m/z 389.1 [MH+].

Example 7

5-[1-{3-(Aminomethyl)benzyl}-3-indolyl]-1-(3-indolyl)-1,3-dihydroimidazol-2-one Trifluoroacetic Acid Salt

The title product, obtained as an off-white solid, was prepared following the procedure of Example 4 starting from N-[3-(bromomethyl)benzyl]phthalimide.

$^1$H-NMR (400 MHz, CD$_3$OD): δ 3.90 (2H, s), 5.05 (2H, s), 6.51 (1H, d, J 7.3 Hz), 6.60 (1H, s), 6.77 (1H, s), 6.84–6.97 (2H, m), 6.99–7.18 (5H, m), 7.18–7.26 (2H, m), 7.31 (1H, s), 7.34 (1H, d, J 8.5 Hz), 7.64 (1H, br d, J 8.0 Hz).

FAB-MS: m/z 434 [MH+].

Example 8

5-[1-(3-Aminopropyl)-3-indolyl]-1-(3-indolyl)-5-methyl-1,3-dihydroimidazol-2-one a) 3-{3-[(2S)-1-(3-Indolyl)-1-oxo-2-proyl]ureido}-1-(ethoxycarbonyl)indole

The sub-title compound was prepared in 50% yield as a white solid following the procedure of Example 1 a) starting from 2S-[1-(3-indolyl)-1-oxopropyl]-2-ammonium chloride.

$^1$H-NMR (400 MHz, DMSO-d$_6$): δ 1.37 (3H, t, J 6.7 Hz), 1.41 (3H, d, J 7.0 Hz), 4.40 (2H, q, J 7.0 Hz), 5.21 (1H, p,

J 7.3 Hz), 6.86 (1H, d, J 7.6 Hz), 7.19–7.27 (2H, m), 7.32 (1H, t, J 7.4 Hz), 7.38 (1H, t, J 7.5 Hz), 7.50 (1H, d, J 6.8 Hz), 7.67 (1H, d, J 7.7 Hz), 7.81 (1H, s), 8.10 (1H, br d, J 7.8 Hz), 8.21 (1H, d, J 7.3 Hz), 8.53 (1H, d, J 3.2 Hz), 8.99(1H, s), 12.11 (1H, br s, indole NH).

FAB-MS: m/z 419 [MH+].

b) The title compound, obtained as a yellow solid, was prepared following the procedure of Example 4 starting from the product of step a). The product was purified by chromatography on silica, eluting with dichloromethane—methanol—ammonium hydroxide (80:20:2), followed by purification by preparative HPLC, C18-reversed phase, acetonitrile—water—trifluoroacetic acid (30:70:0.1).

$^1$H-NMR (500 MHz, CD$_3$OD): δ 1.89 (2H, dt, J 6.8, 15.7 Hz), 2.12 (3H, s), 2.38 (2H, br t, J 8.2 Hz), 4.08 (2H, t, J 6.6 Hz), 6.86 (1H, t, J 7.6 Hz), 6.88 (1H, s), 7.01 (1H, t, J 7.3 Hz), 7.03 (1H, t, J 7.7 Hz), 7.13 (1H, t, J 7.9 Hz), 7.17 (1H, s), 7.19 (1H, d, J 7.9 Hz), 7.28 (1H, d, J 8.2 Hz), 7.31 (1H, d, J 8.2 Hz), 7.39 (1H, d, J 8.0 Hz).

Example 9

5-[1-(3-Hydroxypropyl)-3-indolyl]-1-(3-indolyl)-1,3-dihydroimidazol-2-one

The title compound, obtained as an off-white solid, was prepared following the procedure of Example 4 starting from O-acetyl-3-brompropanol.

$^1$H-NMR (400 MHz, CDCl$_3$): δ 1.61 (2H, p, J 6.2 Hz), 2.77 (2H, t, J 5.7 Hz), 3.95 (2H, t, J 6.4 Hz), 6.41 (1H, s), 6.68 (1H, d, J 2.2 Hz), 7.00 (1H, t, J 7.3 Hz), 7.12–7.37 (7H, m), 7.73 (1H, d, J 7.7 Hz), 8.57 (1H, br s), 8.74 (1H, br s).

FAB-MS: m/z 473.1 [MH+].

Example 10

5-(8-Hydroxymethyl-6,7,8,9-tetrahydropyrido[1,2-a]indol-10-yl)-1-(3-indoyl)-1,3-dihydroimidazol-2-one The title compound, obtained as a off-white solid, was prepared following the procedure of Example 2 starting from 2-(8-acetoxymethyl-6,7,8,9-tetrahydropyrido[1,2-a]indol-10-yl)-2-oxoethylammonium chloride, which latter compound was prepared according to the procedure described by Bergman et al. Tetrahedron 29 (1973) 971–976, starting from acetic acid 6,7,8,9-tetrahydropyridol[1,2-a]indol-8-ylmethyl ester.

$^1$H-NMR (500 MHz, CDO$_3$D): δ 1.55–1.66 (1H, m), 1.70–1.79 (1H, m), 2.05–2.21 (2H, m), 2.91 (1H, dd, J 3.9, 16.4 Hz), 3.33–3.40 (2H, m), 3.72 (1H, dt, J 5.0, 11.6 Hz), 4.13–4.19 (1H, m), 5.50 (1H, s), 6.56 (1H, s), 6.89–6.96 (2H, m), 6.97–7.07 (3H, m), 7.18 (1H, d, J 8.1 Hz), 7.23–7.35 (3H, m).

FAB-MS: m/z 399 [MH+].

Example 11

1-[1-{3-(Aminomethyl)benzyl}-3-indolyl]-5-(1-methyl-3-indolyl)-1,3-dihydroimidazol-2-one Acetic Acid Salt The title compound was prepared following the procedure outlined in Example 3 starting from the product of Example 3 e) and N-[3-(bromomethyl)benzyl]phthalimide.

FAB-MS: m/z 448 [MH+].

Example 12

5-[1-(3-Amidinothiopropyl)-3-indolyl]-1-(3-indolyl)-1,3-dihydroimidazol-2-one Acetic Acid Salt The product from Example 9 (0.062 g, 0.16 mmol), pyridine (0.4 mol) and methanesulphonic anhydride (0.037 g, 0.21 mmol) was dissolved in dichloromethane (30 ml) and stirred for 4 hours at room temperature. The reaction was quenched by treatment of the organic phase with sulfuric acid (1 M, 40 ml). The phases were separated and the organic phase washed with brine (1×40 ml) and dried over Na$_2$SO$_4$. After removal of the solvent in vacuu the crude methanesulphonate was used directly.

The crude methanesulphonate was treated with thiourea (0.025 g, 0.33 mmol) in refluxing absolute ethanol (40 ml) for 18 hours. The solvent was removed and the residue purified by chromatograph on silica. eluting with dichlormethane—methanol—triethylamine (first 90:10:1 then 80:20:1), to give the 5-[1-(3-Amidinothiopropyl)-3-indolyl]-1-(3-indolyl)-1,3-dihydroimidazol-2-one (0.018 g, 25%).

The product was converted to the title compound by dissolving it in acetic acid (1 M) followed by lyophilization.

$^1$H-NMR (400 MHz, DMSO-d$_6$): δ 1.69 (2H, p, J 7.1 Hz), 2.46 (2H, t, J 7.3 Hz), 3.97 (2H, t, J 7.0 Hz), 6.64 (1H, s), 6.75 (1H, s), 6.86 (1H, t, J 7.4 Hz), 6.97–7.15 (4H, m), 7.37 (2H, dd, J 8.2 Hz), 7.41 (1H, s), 7.59 (1H, d, J 8.1 Hz), 10.26 (1H, s), 11.21 (1H, s).

FAB-MS: m/z 431 [MH+].

Example 13

5-(8-Amidinothiomethyl-6,7,8,9-tetrahydropyrido[1,2-a]indol-10-yl)-1-(3-indolyl)-1,3-dihydroimidazol-2-one Acetic Acid Salt The title compound was prepared following the procedure of Example 12 starting from the product of Example 10.

$^1$H-NMR (500 MHz, CDO$_3$D): δ 1.66–1.78 (1H, m), 1.84–1.94 (1H, m), 2.15–2.28 (2H, m), 2.91 (1H, dd, J 7.6, 13.4 Hz), 3.00–3.07 (1H, m), 3.12 (1H, dd, J 7.0, 13.2 Hz), 3.76 (1H, dt, J 5.1, 11.5 Hz), 4.16–4.23 (1H, m), 6.59 (1H, s), 6.93 (1H, t, J 7.8 Hz), 6.98 (1H, t, J 7.8 Hz), 7.03–7.08 (3H, m), 7.21 (1H, d, J 8.0 Hz), 7.28 (2H, d, J 8.4 Hz), 7.38 (1H, d, J 8.0 Hz).

FAB-MS: m/z 457 [MH+].

Example 14

1-(1-Ethoxycarbonyl-3-indolyl)-5-(3-indolyl)-4-methyl-1,3-dihydroimidazol-2-one

The title compound was prepared in 88% yield following the procedure of Example 2 a) starting from the product of Example 8 a).

$^1$H-NMR (400 MHz, DMSO-d$_6$): δ 1.33 (3H, t, J 7.1 Hz), 1.98 (3H, s), 4.39 (2H, q, J 7.1 Hz), 6.90 (1H, t, J 7.3 Hz), 7.01 (1H, t, J 7.9 Hz), 7.09 (1H, t, J 7.4 Hz), 7.18 (1H, d, J 2.6 Hz), 7.23–7.32 (4H, m), 7.58 (1H, s), 7.98 (1H, d, J 8.7 Hz), 10.38 (1H, s, NH), 11.10 (1H, br s, indole NH).

FAB-MS: m/z 401 [MH+].

Example 15

1,5-Bis-(3-indolyl)-4-methyl-1,3-dihydroimidazol-2-one

The title product was prepared following the procedure of Example 2 starting from the product of Example 14. The product was precipitated from diethyl ether.

$^1$H-NMR (400 MHz, DMSO-d$_6$): δ 1.97 (3H, s), 6.87 (2H, t, J 7.6 Hz), 6.96–77.03 (2H, m), 7.17–7.21 (2H, m), 7.25 (2H, t, J 6.8 Hz), 7.28 (1H, d, J 8.4 Hz), 10.16 (1H, s, NH), 10.95 (1H, s, indole NH), 11.02 (1H, s, indole NH).

FAB-MS: m/z 329 [MH+].

Example 16

5-(3-Indolyl)-1-(1-naphthyl)-1,3-dihydroimidazol-2-one

The title compound, obtained as an off-white solid, was prepared in 57% yield following the procedure of Example 2 a) starting from the product of Example 5 a).

$^1$H-NMR (400 MHz, DMSO-d$_6$): δ 6.21 (1H, d, J 2.8 Hz), 6.92 (1H, d, J 2.4 Hz), 6.98 (1H, t, J 6.9 Hz), 7.05 (1H, t, J 6.9 Hz), 7.23 (1H, d., J 8.0 Hz), 7.46–7.59 (5H, m), 7.65 (1H, d, J 7.9 Hz), 8.00 (2H, d, J 7.5 Hz), 10.45 (1H, br s), 10.79 (1H, br s).

FAB-MS: m/z 325 [MH+].

Example 17

1-(3-Benzo[b]thiophenyl)-5-(3-indolyl)-1,3-dihydroimidazol-2-one

The title compound, obtained as a off-white solid, was prepared in 80% yield following the procedure of Example 2 a) starting from the product of Example 6 a).

$^1$H-NMR (400 MHz, CDCl$_3$): δ 6.41 (1H, s), 6.72 (1H, s), 7.11–7.23 (2H, m), 7.27–7.39 (3H, m), 7.43 (1H, s), 7.62 (2H, t, J 7.7 Hz), 7.82 (1H, d J 7.8 Hz), 8.04 (1H, s), 10.42 (1H,

FAB-MS: m/z 332.0 [MH+].

Example 18

1-(1-Ethoxycarbonyl-3-indolyl)-5-(5-methoxy-3-indolyl)-1,3-dihydroimidazol-2-one The title compound was prepared following the procedure of Example 2 a) starting from [2-(5-methoxy-3-indolyl)-2-oxoethyl]ammonium chloride.

$^1$H-NMR (500 MHz, DMSO-d$_6$): δ 1.35 (3H, t, J 7.2 Hz), 3.55 (3H, s), 4.41 (2H, q, J 7.3 Hz), 6.65 (1H, d, J 9.2 Hz), 6.75 (1H, s), 6.85 (1H, s), 6.92 (1H, s), 7.15–7.18 (2H, m), 7.27 (1H, d, J 7.8 Hz), 7.33 (1H t, J 7.1 Hz), 7.73 (1H, s), 8.08 (1H, d, J 9.0 Hz), 10.40 (1H,s), 10.84 (1H, s).

FAB-MS: m/z 417 [MH+].

Example 19

5-[1-{3-(Aminomethyl)benzyl}-3-indolyl]-1-(3-benzo[b]thiophenyl)-4-(ethoxycarbonyl)-2,3-dihydroimidazole-2-one Acetic Acid Salt The title product was prepared as described in Example 9 starting from 2-amino-3-(3-indolyl)-3-oxo-propionic acid methyl ester hydrochloride and 3-azidocarbonyl-benzo-[b]thiophene.

$^1$H-NMR (400 MHz, CD$_3$OD): δ 3.68 (3H, s), 3.88 (2H, s), 5.21 (2H, s), 6.48 (1H, d J 7.2), 6.93 (1H, t J 8.0), 6.98–7.06 (2H, m) 7.09–7.25 (6H, m), 7.26–7.34 (2H, m), 7.45 (1H, d J 7.8), 7.57 (1H, s), 7.78 (1H, d J 8.8).

FAB-MS: m/z: 509.1 [MH+].

Example 20

4-(Ethoxycarbonyl)-5-(1-methyl-3-indolyl)-1-(1-naphthyl)-2,3-dihydroimidazole-2-one The title compound was prepared as described in Example 16 starting from 2-amino-3-(3-indolyl)-3-oxo-propionic acid ethyl ester hydrochloride.

$^1$H-NMR (500 MHz, CDCl$_3$): δ 0.98 (3H, t J 7.1 Hz), 3.49 (3H, s), 4.11–4.20 (2H, m), 6.60 (1H, s), 7.02–7.07 (1H, m), 7.15 (2H, d, J 4.2), 7.30–7.39 (3H, m), 7.46–7.53 (2H, m), 7.74–7.87 (3H, m), 8.87 (1H, br s).

FAB-MS: m/z: 412.2 [MH+], 823.2 [MH2+], 845.1 [MNa2+].

Example 21

1,5-Bis-(3-indolyl)-5-(trifluoromethyl)-1,3-dihydroimidazol-2-one

The title product was prepared following the procedure of Example 2 starting from 2-amino-3,3,3-trifluoro-1-(3-indolyl)-propan-1-one.

$^1$H-NMR (500 MHz, DMSO-d$_6$): δ 6.87–6.93 (2H, m), 7.01 (2H, q, J 7.2 Hz), 7.21–7.27 (3H, m), 7.30–7.36 (3H, m), 11.09 (1H, s), 11.25 (1H, s), 11.45 (1H, s).

FAB-MS: m/z 383 [MH+].

Example 22

1,5-Bis-(3-indolyl)-4-phenyl-1,3-dihydroimidazol-2-one

The title product was prepared following the procedure of Example 2 starting from 2-amino-1-(3-indolyl)-2-phenylethanone hydrochloride.

$^1$H-NMR (400 MHz, DMSO-d$_6$): δ 6.82 (1H, t, J 7.3 Hz), 6.90 (1H, t, J 7.3 Hz), 6.96–7.05 (2H, m), 7.05–7.18 (4H, m), 7.20 (1H, s), 7.22–7.31 (6H, m), 10.87 (1H, s), 11.01 (1H, br s), 11.11 (1H, br s).

FAB-MS: m/z 391 [MH+].

Example 23

5-[1-(3-Aminopropyl)-3-indolyl]-1-(3-indolyl)-4-phenyl-1,3-dihydroimidazol-2-one Trifluoroacetic Acid Salt The title product was prepared following the procedure of Example 4 starting from 2-amino-1-(3-indolyl)-2-phenylethanone hydrochloride.

$^1$H-NMR (400 MHz, CD$_3$OD): δ 1.87 (2H, dt, J 6.7, 15.4 Hz), 2.33 (2H, t, J 8.3 Hz), 4.10 (2H, t, J 8.3 Hz), 6.87–6.95 (2H, m), 6.97 (1H, s), 7.06 (1H, t, J 7.6 Hz), 7.11 (1H, t, J 7.6 Hz), 7.14–7.25 (6H, m), 7.28–7.37 (4H, m).

FAB-MS: m/z 448 [MH+].

Example 24

5-{1-[3-(N,N-Dimethylamino)propyl]-3-indolyl}-1-(3-indolyl)-1,3-dihydroimidazol-2-one Acetic Acid Salt The title compound was prepared following the procedure of Example 2 starting from 3-(N,N-dimethylamino)propyl chloride hydrocloride and the product of Example 1 a).

$^1$H-NMR (500 MHz, CD$_3$OD): δ 1.81 (2H, p, J 7.6 Hz), 1.94 (3H, s), 2.45 (6H, s), 3.98 (2H, t, J 6.6 Hz), 6.58 (1H, s), 6.78 (1H, s), 6.95 (1H, t, J 7.6 Hz), 7.08–7.13 (2H, 7.16–7.22 (2H, m), 7.34 (1H, d, J 8.1 Hz), 7.35 (1H, s), 7.40 (1H, d, J 8.7 Hz), 7.67 (1H, d, J 8.3 Hz).

FAB-MS: m/z 400 [MH+].

Example 25

5-[1-(3-Aminopropyl)-3-indolyl]-1-(4-phenoxyphenyl)-1,3-dihydroimidazol-2-one Acetic Acid Salt The title compound was prepared following the procedure of Example 5 starting from 4-phenoxyphenyl isocyanate.

$^1$H-NMR (500 MHz, CDCl$_3$): δ 1.93 (3H, s), 2.09 (2H, p, J 7.8 Hz), 2.79 (2H, t, J 8.1 Hz), 4.21 (2H, t, J 6.7 Hz), 6.65

(1H, s), 6.89 (4H, d, J 8.7 Hz), 6.92 (1H, s), 7.02 (1H, t, J 6.7 Hz), 7.09 (1H, t, J 6.7 Hz), 7.17–7.22 (3H, m), 7.31 (2H, t, J 8.0 Hz), 7.37 (1H, d, J 8.0 Hz), 7.41 (1H, d, J 8.0 Hz).

FAB-MS: m/z 425 [MH+].

Example 26

1-[1-(4-Aminobutyl)-3-indolyl]-4-(ethoxycarbonyl)-5-(1-methyl-3-indolyl)-1,3-dihydroimidazol-2-one Acetic Acid Salt The title compound was prepared following the procedure outlined in Example 3 starting from 2-amino-3-(1-methyl-3-indolyl)-3-oxopropionic acid ethyl ester hydrochloride (von Geldern et al, J. Med. Chem. 39 (1996) 957–967).

$^1$H-NMR (400 MHz, CDCl$_3$): 0.70 (3H, t, J 7.1 Hz), 1.57 (2H, p, J 7.6 Hz), 1.84 (2H, p, J 7.6 Hz), 2.71 (2H, t, J 7.4 Hz), 3.50 (3H, s), 4.00 (2H, q, J 6.9 Hz), 4.23 (2H, t, J 7.1 Hz), 6.72 (1H, s), 6.73 (1H, s), 6.96 (1H, t, J 7.8 Hz), 7.01–7.09 (2H, m), 7.11–7.19 (3H, m), 7.26 (1H, d, J 8.1 Hz), 7.37 (1H, d, J 7.8 Hz), 9.46 (1H, bs). (obtained for the free amine)

FAB-MS m/z: 472.2 [MH+].

Example 27

5-[1-(3-Aminopropyl)-3-indolyl]-4-carbamoyl-1-(benzo[b]thiophen-3-yl)-2,3-dihydroimidazole-2-one Acetic Acid Salt The title compound was prepared following the procedure outlined in Example 4 starting from 2-amino-3-(1-methyl-3-indolyl)-3-oxopropionic amide hydrochloride prepared in analogy with von Geldern et al. (ibid).

$^1$H-NMR (400 MHz, DMSO-d$_6$): δ 0.95–1.08 (2H, m), 1.48–1.58 (2H, m), 2.43–2.47 (2H, m), 4.03 (2H, t, J 6.3 Hz), 6.95 (1H, t, J 8.2 Hz), 7.10 (1H, t, J 8.2 Hz), 7.21–7.33 (3H, m), 7.35–7.45 (3H, m), 7.86–7.94 (2H, m).

FAB-MS m/z: 428.0 [MH+].

Example 28

5-[3-(Aminopropyl)-3-indolyl]-4-benzyl-1-(3-indolyl)-1,3-dihydroimidazol-2-one Acetic Acid Salt a) 2-(N-tert-Butoxycarbonylamino)-1-{1-[3-(1,3-dioxo-1,3-dihydroisoindol-2-yl)-propyl]-3-indolyl}-3-phenyl-1-propanone 2-(N-tert-butoxycarbonylamino)-1-{1-[3-(1,3-dioxo-1,3-dihydroisoindol-2-yl)-propyl]-3-indolyl}-1-ethanone (0.30 g, 0.65 mmol) was dissolved in dry THF (7.5 ml) and cooled to −10° C. Sodium bis(trimethylsilyl)amide (0.65 ml, 1 M in THF, 0.65 mmol) was added and the resulting yellow solution stirred for 15 minutes. Benzylbromide (0.16 ml, 1.30 mmol) was added and the stirring continued for 15 minutes at −10° C., the cooling bath was removed and stirring continued for 4 hours. Saturated NH$_4$Cl(aq) was added followed by removal of the aqueous phase. The organic solvent was evaporated in vacuum and the residue chromatographed furnishing the sub-title product (0.28 g, 79%).

$^1$H-NMR (400 MHz, CDCl$_3$): δ 1.42 (9H, s), 2.21 (2H, p, J 6.9 Hz), 3.13–3.25 (1H, dd, J 6.0, 13.6), 3.21 (1H, dd, J 7.3, 13.5), 3.73 (2H, t, J 6.4 Hz), 4.07–4.20 (2H, m), 5.17–5.24 (1H, m), 5.58 (1H, br d, J 7.8 Hz, NH), 7.10–7.23 (5H, m), 7.29–7.35 (3H, m), 7.73 (1H, s), 7.75–7.80 (2H, m), 7.85–7.92 (2H, m), 8.34–8.40 (1H, m).

APCI-MS: M/z 452.2 [MH-CO$_2^t$Bu]

b) (2-{1-[3-(1,3-dioxo-1,3-dihydroisoindol-2-yl)-propyl]-3-indolyl}-2-oxo-3-phenylpropyl)ammonium chloride The product of step a) (0.15 g, 0.27 mmol) was dissolved in HCl(EtOAc) (3 ml, 3 M) and stirred for 15 minutes. The solvent was removed furnishing the sub-title product (0.13 g, quant) as a white solid.

$^1$H-NMR (400 MHz, CD$_3$OD): δ 2.23 (2H, p, J 6.6 Hz), 3.22 (1H, dd, J 7.31. 13.8 Hz), 3.39 (1H, dd, J 7.11, 13.8 Hz), 3.68 (2H, t, J 6.7 Hz), 4.25 (2H, t, J 6.9 Hz), 4.96 (1H, t, J 7.3 Hz), 7.19–7.35 (7H, m), 7.52 (1H, d, J 8.1 Hz), 7.80–7.89 (4H, m), 8.07 (1H, s), 8.25 (1H, d, J 7.72 Hz).

c) 3-[3-(2-{1-[3-(1,3-dioxo-1,3-dihydroisoindol-2-yl)-propyl]-3-indolyl}-2-oxo-3-phenylpropyl)ureido]-1-(ethoxycarbonyl)indole The sub-title product was prepared in 58% yield as a yellow solid following the procedure of Example 1 a) starting from the product of step b).

APCI-MS: m/z 682.1 [MH+]

d) 4-benzyl-5-{-1-[3-(1,3-dioxo-1,3-dihydroisoindol-2-yl)-propyl]-3-indolyl}-1-[1-(ethoxycarbonyl)-3-indolyl]-1,3-dihydroimidazol-2-one The product of step c) (0.11 g, 0.16 mmol) and scandium (III)triflate (0.06 g, 0.012 mmol) was dissolved in methanol (6 ml). The reaction mixture was heated to 110° C. in a sealed tube for 3.5 hours. The methanol was removed and the residue dissolved in ethyl acetate and filtered through SiO$_2$, the sub title product (0.080 g, 78%) was obtained after removal of solvent.

$^1$H-NMR (400 MHz, DMSO-d$_6$): δ 1.25 (3H, t, J 7.1 Hz), 1.85 (2H, p, J 6.7 Hz), 3.14 (2H, t, J 7.0 Hz), 3.71 (2H, s), 4.15 (2H, t, J 6.5 Hz), 4.27 (2H, q, J 7.2 Hz), 6.92 (1H, t, J 7.5 Hz), 7.03–7.09 (2H, m), 7.12–7.24 (4H, m), 7.26–7.37 (4H, m), 7.40 (1H, d, J 8.2 Hz), 7.45 (1H, s), 7.62 (1H, s), 7.82–7.89 (5H, m).

APCI-MS: m/z 664.1 [MH+]

e) The title product, obtained as an off-white solid, was prepared in 57% yield following the procedure of Example 4 b) starting from the product of step d).

$^1$H-NMR (400 MHz, DMSO-d$_6$): δ 1.64 (2H, p, J 6.6 Hz), 1.86 (3H, s), 2.21 (1H, t, J 6.7 Hz), 3.66 (2H, s), 4.10 (2H, t, J 6.7 Hz), 6.82–6.91 (2H, m), 6.96–7.05 (2H, m), 7.16–7.32 (10H, m), 7.35 (1H, d, J 8.3 Hz), 10.29 (1H, br s, NH), 11.01 (1H, br s, NH).

FAB-MS: m/z 462.2 [MH+]

Example 29

5-[3-(Aminopropyl)-3-indolyl]-1-(3-indolyl)-4-[(N-methylcarboxamid)methyl]-1,3-dihydroimidazol-2-one Trifluoroacetic Acid Salt The title product, obtained as an off-white solid, was prepared following the procedure of Example 28, with the exception that acetic acid was used instead of scandiumtriflate/methanol, starting from 2-(N-tert-butoxycarbonylamino)-1-{1-[3-(1,3-dioxo-1,3-dihydroisoindol-2-yl)-propyl]-3-indolyl}-1-ethanone and ethyl bromacetate.

FAB-MS: m/z 443.3 [MH+]

Abbreviations

Boc=butoxycarbonyl group
DMF=N,N-Dimethyl formamide
t-Boc=t-butoxycarbonyl group
THF=tetrahydrofuran
triflate=trifluoromethane sulfonate
Troc=trichloroethoxy carbonyl group

What is claimed is:

1. A compound of formula (II'):

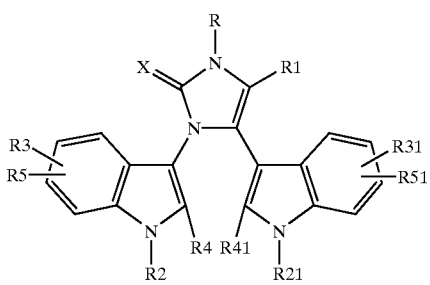

(II')

wherein:
X is O or S,
R is H, OH, NH$_2$, C$_{1-6}$alkyl, hydroxyC$_{1-6}$alkyl, aminoC$_{1-6}$alkyl,
R1 is H, C$_{1-6}$alkyl, fluoro substituted C$_{1-6}$alkyl, phenyl, benzyl, carboC$_{1-6}$alkoxy, carbobenzyloxy, carbohydroxy, carbamoyl, or methyl(N-C$_{1-6}$alkylcarbamoyl),
R2 and R21 are, independently, H, C$_{1-6}$alkyl, haloC$_{1-6}$alkyl, benzyl, C$_{1-3}$alkoxy substituted benzyl, nitrile C$_{1-6}$alkyl, hydroxyC$_{1-6}$alkyl, aminoC$_{1-6}$alkyl, (pyridinylmethyl)aminoC$_{1-6}$alkyl, (mono- or di-C$_{1-6}$alkyl)aminoC$_{1-6}$alkyl, (mono- or di-C$_{1-3}$haloalkyl)aminoC$_{1-6}$alkyl, aminoC$_{3-7}$cycloalkyl, (mono- or di-C$_{1-6}$alkyl)aminoC$_{3-7}$cycloalkyl, (aminoC$_{3-7}$cycloalkyl)C$_{1-3}$alkyl, (hydroxyC$_{1-6}$alkyl)aminoC$_{1-6}$alkyl, (aminoC$_{1-6}$alkyl)aminoC$_{1-6}$alkyl, (C$_{1-6}$alkynyl)aminoC$_{1-6}$alkyl, (benzyl)aminoC$_{1-6}$alkyl, (mono- or di-C$_{1-3}$alkoxy substituted benzyl)aminoC$_{1-6}$alkyl, (aminoC$_{1-3}$alkylphenyl)C$_{1-3}$alkyl, (aminoC$_{1-3}$alkylthiophenyl)C$_{1-3}$alkyl, (aminoC$_{1-3}$alkylpyridinyl)C$_{1-3}$alkyl, guanidino C$_{1-6}$alkyl, (guanidinoC$_{1-3}$alkylphenyl)C$_{1-3}$alkyl, amidinoC$_{1-6}$alkyl or amidinothioC$_{1-6}$alkyl;
R3, R31, R5 and R51 are each independently H, halogen, C$_{1-6}$alkyl, haloC$_{1-6}$alkyl, hydroxyC$_{1-6}$alkyl, C$_{1-6}$alkoxy, hydroxy, amino, nitro or nitrile, and R4 and R41 are, independently, H, C$_{1-3}$alkyl or together with R2 or R21, form an annulated ring which may be substituted by hydroxyC$_{1-3}$alkyl, amidinothioC$_{1-3}$alkyl, or aminoC$_{1-3}$alkyl,
or a salt thereof, a solvate thereof, or a solvate of a salt thereof.

2. A compound according to claim 1, wherein each indolyl, independently, is substituted with a group selected from the group consisting of aminopropyl, dimethylaminopropyl, aminobutyl, aminocyclopentyl, aminomethylbenzyl and amidinothiopropyl.

3. A compound according to claim 1, in which X is O and R is H.

4. A compound according to claim 1, in which
R1 is H, methyl or a fluoro substituted C$_{1-6}$alkyl, and
R3, R31, R5 and R51 are independently H or methoxy.

5. A compound according to claim 1, in which when R4 or R41 is H, R2 or R21 is H, methyl, hydroxyC$_{1-6}$alkyl, aminoC$_{1-6}$alkyl, (mono- or di-C$_{1-6}$alkyl)aminoC$_{1-6}$alkyl, aminoC$_{3-7}$cycloalkyl, (mono- or di-C$_{1-6}$alkyl)aminoC$_{3-7}$cycloalkyl, guanidino C$_{1-6}$alkyl, amidinoC$_{1-6}$alkyl or amidinothioC$_{1-6}$alkyl, or when R2 and R4 or R21 and R41 together form an annulated ring, they together comprise 4 or 5 carbons.

6. The compounds:
5-[1-(3-Aminopropyl)-3-indolyl]-1-(3-indolyl)-1,3-dihydroimidazol-2-one,
5-[1-{3-(Aminomethyl)benzyl}-3-indolyl]-1-(3-indolyl)-1,3-dihydroimidazol-2-one,
5-[1-(3-Aminopropyl)-3-indolyl]-1-(3-indolyl)-4-methyl-1,3-dihydroimidazol-2-one,
5-[1-(3-Amidinothiopropyl)-3-indolyl]-1-(3-indolyl)-1,3-dihydroimidazol-2-one,
5-{1-[3-(N,N-Dimethylamino)propyl]-3-indolyl}-1-(3-indolyl)-1,3-dihydroimidazol-2-one, and
5-[1-(3-Aminopropyl)-3-indolyl]-1-(3-indolyl)-4-phenyl-1,3-dihydroimidazol-2-one,
or a salt or solvate thereof or a solvate of a salt thereof.

7. A pharmaceutically acceptable salt of a compound as claimed in claim 1.

8. A pharmaceutical formulation comprising a compound as claimed in claim 1 or a pharmaceutically acceptable salt thereof as active ingredient, and a pharmaceutically acceptable adjuvant, diluent and/or carrier therefor.

9. A process for the synthesis of a compound of formula (II') as defined in claim 1, comprising intramolecular condensation of a compound of formula (IV')

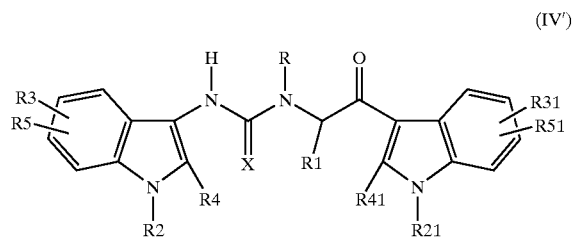

(IV')

in which X, R, R1, R2, R3, R4, R5, R21, R31, R41 and R51 are as defined in claim 1.

10. A process according to claim 9, wherein the condensation is performed under acidic conditions, at a temperature in the range of from about 90° C. to about 130° C., for a period of time in the range of from about 5 min to about 6 h.

11. A process for the synthesis of a compound of formula (II') as defined in claim 1, in which X is O, comprising synthesizing by intramolecular condensation of a compound of formula (V')

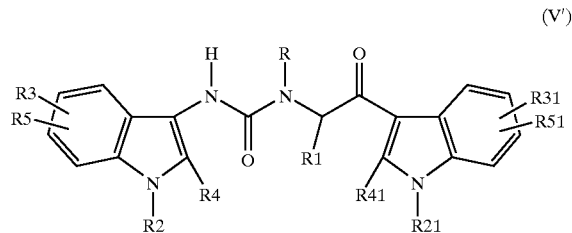

(V')

in which R, R1, R2, R3, R4, R5, R21, R31, R41 and R51 are as defined in claim 1.

12. A process for the synthesis of a compound of formula (V') as defined in claim 11, in which R2 and R21 are not H, comprising alkylating, with an optionally substituted alkylating agent, a compound of formula (VII')

(VII')

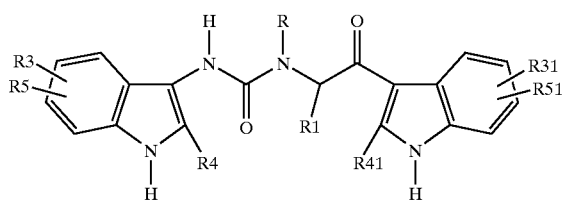

in which R, R1, R3, R4, R5, R31, R41 and R51 are as defined in claim 11.

13. A process according to claim 12, wherein the alkylating agent is selected from the group consisting of alkyl halides, alkyl halides carrying a dialkyl amino group and alkylating agents carrying a protected amino or hydroxy group.

14. A process for the synthesis of a compound of formula (II') as defined in claim 1, in which at least one of R2, R21 or an indoyl carries an amino or hydroxy group, and pharmaceutically acceptable salts thereof, comprising deprotecting a compound of formula (II'), in which at least one of R2, R21 or an indoyl carries a protected amino or hydroxy group.

15. A process for the synthesis of a compound of formula (II') as defined in claim 1, in which X is O, R2 is alkyl and each indoyl, independently, is substituted on the indole nitrogen with an alkyl carrying an amino or hydroxy group, comprising deprotecting a compound of formula (IX')

(IX')

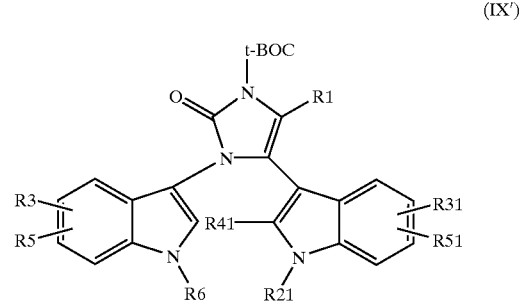

in which R6 is an alkyl carrying a protected amino or hydroxy group, t-Boc is a t-butoxycarbonyl group and R1, R21, R3, R31, R4, R41, R5 and R51 are as defined in claim 1.

16. A method of treating an inflammatory or bronchopulmonary disorder comprising administering to an individual requiring such treatment, a therapeutically effective amount of a compound of claim 1.

* * * * *

UNITED STATES PATENT AND TRADEMARK OFFICE
CERTIFICATE OF CORRECTION

PATENT NO. : 6,492,409 B1
DATED : December 10, 2002
INVENTOR(S) : Peter Sjö, Matti Lepistö and Kostas Karabelas It is certified that error appears in the above-identified patent and that said Letters Patent is hereby corrected as shown below:

Title page,
Item [30], Foreign Application Priority Data, replace "990237" with -- 9902387-1 --.
Item [56], FOREIGN PATENT DOCUMENTS, 2nd reference, replace "7/1990" with -- 7/1990 (Abstract Only) --.

Column 9,
Line 67, replace "." after sucrose with -- , --.

Column 10,
Line 39, after "in" insert -- the --.

Column 12,
Line 37, replace "save" with -- gave -- after (100:10).
Lines 49 and 50, replace "Trifluoroacetic Acid Salt" with -- trifluoroacetic acid salt --.
Line 67, replace "I" before "b)" with -- 1 --.

Column 13,
Line 7, do not indent after "c)".
Line 18, replace "mi/z" with -- m/z --.

Column 14,
Line 12, replace "freez" with -- freeze --.
Line 24, replace "Trifluoroacetic Acid Salt" with -- trifluoroacetic acid salt --.
Line 63, replace "7.0" with -- 7.00 --.

Column 15,
Line 3, replace "Trifluoroacetic Acid Salt" with -- trifluoroacetic acid salt --.
Lines 58 & 59, replace "Acetic Acid Salt" with -- acetic acid salt --.

Column 16,
Lines 45 & 46, replace "Trifluoroacetic Acid Salt" with -- trifluoroacetic acid salt --.

Column 17,
Line 37, replace "a" with -- an --.
Lines 55 to 56, replace "Acetic Acid Salt" with -- acetic acid salt --.
Line 65, replace "Acetic Acid Salt" with -- acetic acid salt --.

UNITED STATES PATENT AND TRADEMARK OFFICE
CERTIFICATE OF CORRECTION

PATENT NO. : 6,492,409 B1
DATED : December 10, 2002
INVENTOR(S) : Peter Sjö, Matti Lepistö and Kostas Karabelas It is certified that error appears in the above-identified patent and that said Letters Patent is hereby corrected as shown below:

Column 18,
Line 11, replace "silica." with -- silica, --.
Line 29, replace "Acetic Acid Salt" with -- acetic acid salt --.
Line 64, replace "77.03" with -- 7.03 --.

Column 19,
Line 20, replace "a" with -- an --.
Line 26, insert -- s). -- after "1H".
Line 47, replace "Acetic Acid Salt" with -- acetic acid salt --.

Column 20,
Lines 33 & 34, replace "Trifluoroacetic Acid Salt" with -- trifluoroacetic acid salt --.
Lines 47 & 48, 62 & 63, replace "Acetic Acid Salt" with -- acetic acid salt --.
Line 55, insert -- m), -- after "2H".
Line 65, replace "4-phenoxyphenyl isocyanate" with -- 4-phenoxyphenylisocyanate --.

Column 21,
Lines 10, 29 & 44, replace "Acetic Acid Salt" with -- acetic acid salt --.

Column 22,
Line 19, replace "5-{-1" with -- 5-{1 --.
Line 40, replace "2.21 (1H" with -- 2.21(2H --.
Line 50, replace "Trifluoroacetic Acid Salt" with -- trifluoroacetic acid salt --.

Signed and Sealed this

Twelfth Day of August, 2003

JAMES E. ROGAN
*Director of the United States Patent and Trademark Office*